(12) United States Patent
Okumura

(10) Patent No.: US 11,890,126 B2
(45) Date of Patent: Feb. 6, 2024

(54) RADIATION IMAGING APPARATUS

(71) Applicant: Shimadzu Corporation, Kyoto (JP)

(72) Inventor: Hiroshi Okumura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 700 days.

(21) Appl. No.: 17/050,169

(22) PCT Filed: Mar. 14, 2019

(86) PCT No.: PCT/JP2019/010451
§ 371 (c)(1),
(2) Date: Oct. 23, 2020

(87) PCT Pub. No.: WO2019/208006
PCT Pub. Date: Oct. 31, 2019

(65) Prior Publication Data
US 2021/0369229 A1 Dec. 2, 2021

(30) Foreign Application Priority Data

Apr. 26, 2018 (JP) ................................. 2018-085311

(51) Int. Cl.
*A61B 6/00* (2006.01)
*G06T 7/70* (2017.01)

(52) U.S. Cl.
CPC .............. *A61B 6/545* (2013.01); *A61B 6/468* (2013.01); *A61B 6/488* (2013.01); *G06T 7/70* (2017.01);
(Continued)

(58) Field of Classification Search
CPC ........... A61B 6/586; A61B 6/545; A61B 6/54; A61B 6/468; A61B 6/488; A61B 6/46;
(Continued)

(56) References Cited

U.S. PATENT DOCUMENTS

2002/0080921 A1* 6/2002 Smith .................. A61B 6/4291
378/189
2016/0206273 A1* 7/2016 Fukuda .................. A61B 6/463
(Continued)

FOREIGN PATENT DOCUMENTS

JP   H04-341247 A   11/1992
JP   2011-045709 A   3/2011
(Continued)

OTHER PUBLICATIONS

Notice of Allowance dated Apr. 18, 2023 for corresponding Japanese Patent Application No. 2020-516093.
(Continued)

*Primary Examiner* — Irakli Kiknadze
(74) *Attorney, Agent, or Firm* — Muir Patent Law, PLLC

(57) ABSTRACT

A controller (50) is provided with: an orientation determination unit (51) configured to determine an orientation of a subject; a protocol acquisition unit (52); an annotation processing unit (53) configured to perform annotation; a difference determination unit (54) configured to determine whether the currently selected protocol and the orientation of the subject determined by the orientation determination unit (51) are inconsistent with each other; and a warning unit (55) configured to issue a warning and an imaging prohibition unit (56) configured to prohibit imaging when the difference determination unit (54) determines that the currently selected protocol among the protocols acquired by the protocol acquisition unit (52) and the orientation of the subject determined by the orientation determination unit (51) are inconsistent with each other.

22 Claims, 10 Drawing Sheets

(52) U.S. Cl.
CPC .............. *G06T 2207/10028* (2013.01); *G06T 2207/20084* (2013.01); *G06T 2207/30201* (2013.01)

(58) Field of Classification Search
CPC ......... A61B 5/0077; A61B 6/04; A61B 6/461; A61B 6/5211; A61B 6/4464; A61B 6/463; A61B 6/56; A61B 6/025; A61B 6/5223; A61B 6/465; A61B 6/5241; A61B 6/563; A61B 34/10; A61B 34/25; A61B 2034/104; A61B 2034/105; A61B 2034/108; A61B 5/742; A61B 5/055; A61B 6/4435; A61B 6/035; A61B 6/0414; A61B 6/4208; A61B 6/4258; A61B 6/589; A61B 6/48; A61B 6/544; A61B 5/70; A61B 6/0407; A61B 6/032; A61B 6/4441; A61B 6/42; A61B 6/4429; A61B 6/44; A61B 6/542; G06T 7/70; G06T 2207/20084; G06T 2207/30201; G06T 2207/10028; G06T 11/003; G06T 7/0012; G06T 2207/10116; G06T 2207/30068; G06T 17/00; G06T 19/20; G06T 19/003; G06T 2210/41; G06T 2219/2021; G06T 2207/20016; G06T 2207/30004; G06T 11/008; G06T 7/80; G06T 15/08; G06T 7/11; G06T 19/00; G06T 2207/10081; G06T 2207/30008; G06T 2207/30016; G06T 2207/10072; G06T 2207/20081; G06T 2207/10088; G16H 40/63; G16H 30/20; G06F 19/321; G06V 10/25; G01R 33/30

USPC .......................................................... 378/62
See application file for complete search history.

(56) References Cited

U.S. PATENT DOCUMENTS

| | | | |
|---|---|---|---|
| 2017/0354385 A1* | 12/2017 | Lerch | A61B 6/4435 |
| 2018/0021006 A1 | 1/2018 | Takasawa | |
| 2021/0007701 A1* | 1/2021 | Ten Cate | G16H 30/20 |

FOREIGN PATENT DOCUMENTS

| | | |
|---|---|---|
| JP | 2014-171719 A | 9/2014 |
| JP | 2015-173923 A | 10/2015 |
| JP | 2015-130906 A | 7/2017 |
| JP | 2018011871 A | 1/2018 |

OTHER PUBLICATIONS

Written Opinion of the International Searching Authority for PCT application No. PCT/JP2019/010451, dated May 28, 2019, submitted with a machine translation.

First Office Action dated Jun. 29, 2023 issued for the corresponding Chinese Patent Application No. 201980028283.1.

Third Office Action dated Aug. 2, 2022 for corresponding Japanese Patent Application No. JP 2020-516093, submitted with a machine translation.

Second Office Action dated Mar. 8, 2022 for corresponding Japanese Application No. JP 2020-516093.

Notice of Rejection dated Dec. 20, 2022 for corresponding Japanese Patent Application No. JP 2020-516093.

* cited by examiner

AP

RADIATION IMAGING APPARATUS

TECHNICAL FIELD

The present invention relates to a radiation imaging apparatus, such as, e.g., an X-ray imaging apparatus.

BACKGROUND OF THE INVENTION

For example, in general chest X-ray imaging, there are front imaging in which imaging is performed from a front side of a subject and side imaging in which imaging is performed from the lateral side of the subject. The front imaging includes PA (Posterior-Anterior) imaging in which imaging is performed from the back side of the subject and AP (Anterior-Posterior) imaging in which imaging is performed from the front side of the subject. The side imaging includes LR (Left-Right) imaging in which imaging is performed from the left side of the subject and RL (Right-Left) imaging in which imaging is performed from the right side of the subject.

FIG. 5 to FIG. 8 are schematic diagrams each showing the state of performing chest X-ray imaging on a subject M. FIG. 9 to FIG. 12 are schematic diagrams each showing an X-ray image captured by chest X-ray imaging shown in FIG. 5 to FIG. 8.

FIG. 5 shows a state of performing chest X-ray imaging with PA for the subject M. At this time, an X-ray detection unit 33 is arranged on the front side of the subject M, and an X-ray irradiation unit is arranged on the back side of the subject M. The X-rays emitted from the X-ray irradiation unit pass through the subject from the back side to the front side of the subject M, and are detected by the X-ray detection unit 33. FIG. 9 shows the X-ray image taken at this time.

FIG. 6 shows a state of performing chest X-ray imaging with AP for the subject M. At this time, the X-ray detection unit 33 is arranged on the back side of the subject M, and the X-ray irradiation unit is arranged on the front side of the subject M. The X-rays emitted from the X-ray irradiation unit pass through the subject M from the front side of the subject M toward the back side thereof, and are then detected by the X-ray detection unit 33. FIG. 10 shows the X-ray image taken at this time.

FIG. 7 shows a state of performing chest X-ray imaging with LR for the subject M. At this time, the X-ray detection unit 33 is arranged on the right side of the subject M, and the X-ray irradiation unit is arranged on the left side of the subject M. The X-rays emitted from the X-ray irradiation unit pass through the subject from the left side to the right side of the subject M, and are detected by the X-ray detection unit 33. FIG. 11 shows the X-ray image taken at this time.

FIG. 8 shows a state of performing chest X-ray imaging with RL for the subject M. At this time, the X-ray detection unit 33 is arranged on the left side of the subject M, and the X-ray irradiation unit is arranged on the right side of the subject M. The X-rays emitted from the X-ray irradiation unit pass through the subject from the right side to the left side of the subject M, and are then detected by the X-ray detection unit 33. FIG. 12 shows the X-ray image taken at this time.

Note that the mark shown at the lower right of the X-ray image in each of FIG. 9 to FIG. 12 is an annotation indicating the imaging direction.

Patent Document 1 discloses, in the technical field of an X-ray computed tomography (CT) or magnetic resonance imaging (MRI), a medical diagnostic imaging apparatus in which an image of a subject transferred via a top board with respect to a gantry is captured and a posture of the subject, such as, e.g., a supine state and a lateral state, or a body orientation of the subject about whether the subject is to be transferred from a head side or a foot side is determined.

Further, Patent Document 2 discloses an X-ray image capturing apparatus in which a change in the body posture is detected by a vibration sensor or the like and imaging is performed when it is determined that the body posture is as instructed.

PRIOR ART DOCUMENT

Patent Document
Patent Document 1: Japanese Unexamined Patent Application Publication No. 2011-45709
Patent Document 2: Japanese Unexamined Patent Application Publication No. 2014-171719

SUMMARY OF THE INVENTION

Problems to be Solved by the Invention

Such chest X-ray imaging is generally performed by a set of imaging from a plurality of directions with respect to one subject. For example, X-ray imaging is performed as one set of chest front (PA) imaging and chest side (LR or RL) imaging. In this instance, in the imaging protocol list of the target subject, two protocols, i.e., a protocol for imaging the chest from the front and a protocol for imaging the chest from the side, are arranged, and the imaging is performed in order. However, depending on the state of the subject, the order of imaging is sometimes changed at the discretion of the radiologist. In such cases, the radiologist manually selects a menu to be performed from the protocol list displayed on a touch panel or the like, and then performs the imaging. At this time, the radiologist manually selects the protocol and therefore sometimes makes a selection mistake or forgets to make a selection itself. In such cases, it is necessary not only to perform re-selection but also to perform re-imaging when the imaging was performed with a wrong protocol.

Also, in such an X-ray imaging apparatus, for the purpose of easily determining the direction from which the X-ray image was captured, a mark corresponding to the orientation of the subject is sometimes annotated with respect to the captured X-ray image. Such annotation is performed by image processing in a digital imaging apparatus or by placing a physical marker made of metal such as lead in the irradiation field. Such annotation is usually performed by a radiologist or the like, and therefore, a marking mistake or the like sometimes occurs.

The present invention has been made to solve the above-mentioned problems, and an object thereof is to provide a radiation imaging apparatus capable of performing appropriate X-ray imaging by automatically determining whether an orientation of a subject is an orientation for performing front imaging or an orientation for performing side imaging.

Means for Solving the Problem

The present invention as recited in claim 1 is directed to a radiation imaging apparatus for producing a radiographic image of a subject. The apparatus includes: a radiation irradiation unit configured to irradiate the subject with radiation; a radiation detection unit configured to detect the radiation emitted from the radiation irradiation unit and passed through the subject; and an orientation determination unit configured to determine whether an orientation of the subject is an orientation for performing front imaging or an orientation for performing side imaging.

According to the present invention as recited in claim 2, in the invention recited in claim 1, the apparatus further includes an image acquisition unit configured to acquire a visible image of the subject or a range image of the subject. The determination unit determines the orientation of the subject based on the visible image of the subject or the range image of the subject acquired by the image acquisition unit.

According to the present invention as recited in claim 3, in the invention recited in claim 2, the orientation determination unit determines whether the orientation for performing the front imaging is an orientation for performing AP (Anterior-Posterior) imaging or an orientation for performing PA (Posterior-Anterior) imaging, and also determines whether the orientation of performing the side imaging is an orientation for performing RL (Right-Left) imaging or an orientation for performing LR (Left-Right) imaging.

According to the present invention as recited in claim 4, in the invention recited in claim 2, the image acquisition unit is attached to the radiation irradiation unit.

According to the present invention as recited in claim 5, in the invention recited in claim 2, the apparatus further includes: a protocol acquisition unit configured to acquire an imaging protocol for the subject; and a difference determination unit configured to determine whether a currently selected protocol among protocols acquired by the protocol acquisition unit and the orientation of the subject determined by the orientation determination unit are inconsistent with each other.

According to the present invention as recited in claim 6, in the invention recited in claim 5, the apparatus further includes a warning unit configured to issue a warning when the difference determination unit determines that the currently selected protocol among the protocols acquired by the protocol acquisition unit and the orientation of the subject determined by the orientation determination unit are inconsistent with each other.

According to the present invention as recited in claim 7, in the invention recited in claim 5, the radiation imaging apparatus further includes an imaging prohibition unit configured to prohibit radiation imaging for the subject when the difference determination unit determines that the currently selected protocol among the protocols acquired by the protocol acquisition unit and the orientation of the subject determined by the orientation determination unit are inconsistent with each other.

According to the present invention as recited in claim 8, in the invention recited in claim 5, the radiation imaging apparatus further includes an imaging condition changing unit configured to change a radiation imaging condition for the subject when the difference determination unit determines that the currently selected protocol among the protocols acquired by the protocol acquisition unit and the orientation of the subject determined by the orientation determination unit are inconsistent with each other.

According to the present invention as recited in claim 9, in the invention recited in claim 5, the radiation imaging apparatus further includes a protocol replacement unit configured to select a protocol consistent with the orientation of the subject determined by the orientation determination unit among the protocols acquired by the protocol acquisition unit when the difference determination unit determines that the currently selected protocol among the protocols acquired by the protocol acquisition unit and the orientation of the subject determined by the orientation determination unit are inconsistent with each other.

According to the present invention as recited in claim 10, in the invention recited in claim 9, the protocol replacement unit issues a warning when there exists no protocol consistent with the orientation of the subject determined by the orientation determination unit among the protocols acquired by the protocol acquisition unit.

According to the present invention as recited in claim 11, in the invention recited in claim 1, the radiation imaging apparatus further includes an annotation processing unit configured to annotate a mark corresponding to the orientation of the subject for an X-ray image based on the orientation of the subject determined by the orientation determination unit.

According to the present invention as recited in claim 12, in the invention recited in claim 1, the orientation determination unit determines the orientation of the subject by using a neural network.

According to the present invention as recited in claim 13, in the invention recited in claim 2, the orientation determination unit determines the orientation of the subject by using a visible image of a face region of the subject or a range image of the subject acquired by the camera.

Effects of the Invention

According to the invention as recited in claim 1, it is automatically determined whether the orientation of the subject is an orientation for performing front imaging or an orientation for performing side imaging, and therefore appropriate X-ray imaging can be performed.

According to the invention as recited in claim 2, it is possible to determine the orientation of the subject based on the visible image of the subject or the range image of the subject obtained by the image acquisition unit.

According to the invention as recited in claim 3, it is possible to determine whether the orientation for performing the front imaging is an orientation for performing AP (Anterior-Posterior) imaging or an orientation for performing PA (Posterior-Anterior) imaging, and also determines whether the orientation of performing the side imaging is an orientation for performing RL (Right-Left) imaging or an orientation for performing LR (Left-Right) imaging.

According to the invention as recited in claim 4, it is possible to move the imaging range of the subject by the image acquisition unit in conjunction with the moving of the radiation irradiation unit for radiation imaging. Therefore, it is possible to always make the imaging region of the image acquisition unit in consistent with the orientation of the subject.

According to the invention as recited in claim 5, it is possible to make the difference determination unit determine whether the currently selected protocol and the orientation of the subject are inconsistent with each other.

According to the invention as recited in claim 6, a warning is issued when it is determined that the currently selected protocol and the orientation of the subject are inconsistent with each other. Therefore, it is possible to prevent erroneous radiation imaging from being performed.

According to the invention as recited in claim 7, imaging is prohibited when it is determined that the currently selected protocol and the orientation of the subject are inconsistent with each other. Therefore, it is possible to prevent erroneous radiation imaging from being performed.

According to the invention as recited in claim 8, the radiation imaging condition is changed when it is determined that the currently selected protocol and the orientation of the subject are inconsistent with each other. Therefore, it is possible to select a correct radiation imaging condition to thereby prevent erroneous radiation imaging from being performed.

According to the invention as recited in claim 9, the radiation imaging condition is changed when it is determined that the currently selected protocol and the orientation of the subject are inconsistent with each other. Therefore, it is possible to select a correct protocol to thereby prevent erroneous radiation imaging from being performed.

According to the invention as recited in claim 10, a warning is issued when there exists no protocol consistent with the orientation of the subject. Therefore, it is possible to prevent erroneous radiation imaging from being performed.

According to the invention as recited in claim 11, a mark corresponding to the orientation of the subject for an X-ray image is annotated based on the orientation of the subject determined by the orientation determination unit. Therefore, it is possible to automatically perform correct annotation.

According to the invention as recited in claim 12, a neural network is used. Therefore, it is possible to more accurately determine the orientation of the subject.

According to the invention as recited in claim 13, the orientation of the subject is determined by using the visible image of the face region of the subject or the range image of the subject. Therefore, the orientation of the subject can be determined more accurately.

EMBODIMENTS FOR CARRYING OUT THE INVENTION

Hereinafter, some embodiments of the present invention will be described with reference to the attached drawings.

Figure 1:
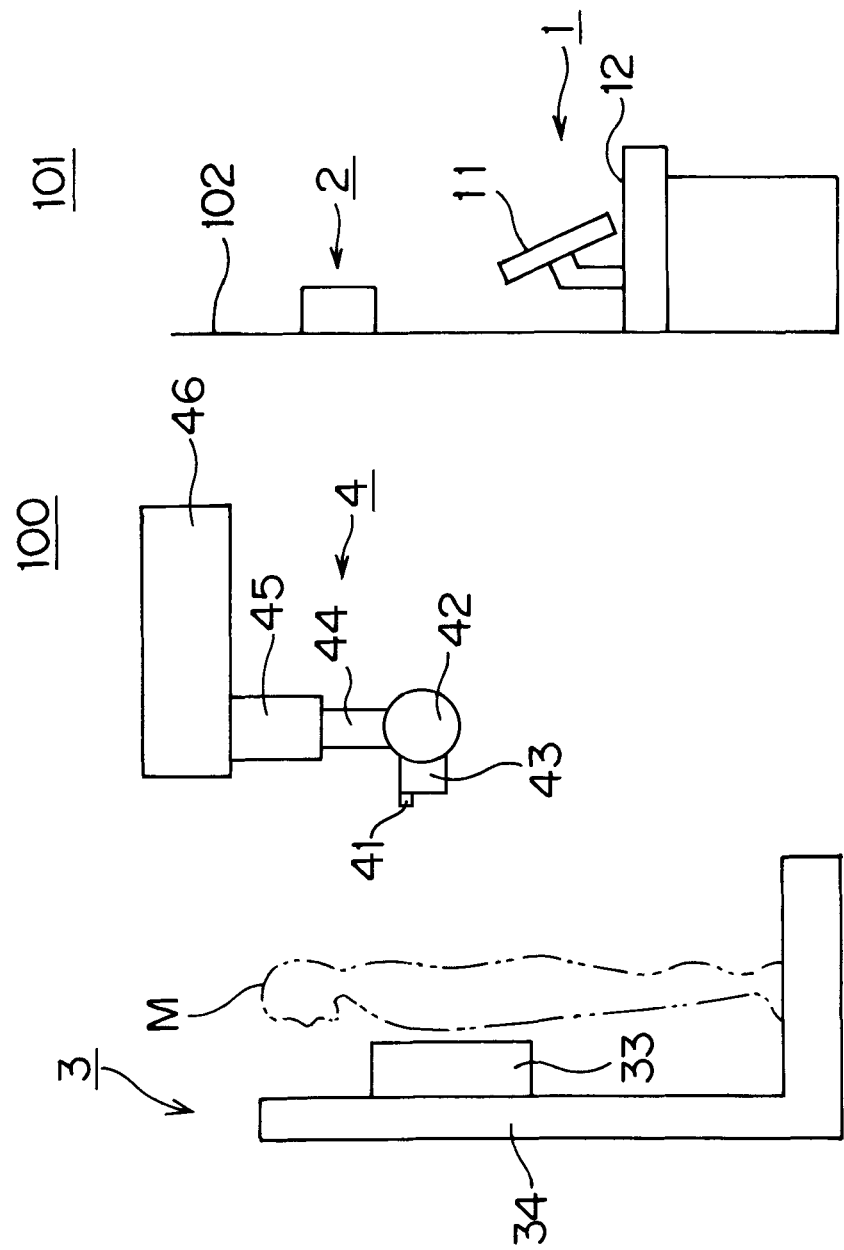
FIG. 1 is a schematic diagram of an X-ray imaging apparatus as a radiation imaging apparatus according to the present invention.

FIG. 1 is a schematic diagram of an X-ray imaging apparatus as a radiation imaging apparatus according to the present invention.

The X-ray imaging apparatus is provided with: a console unit 1 and a high voltage device 2 provided in an operation room 101 in which an operator performs X-ray imaging operations; and a standing posture imaging stand 3 and an imaging unit 4 provided in an imaging room 100 in which imaging is performed on a subject M. The imaging room 100 and the operation room 101 are shielded by a partition wall 102.

The console unit 1 is provided with a display unit 11 composed of a liquid crystal display and the like, and an operation unit 12 composed of a keyboard, a mouse and the like for performing various operations. An X-ray image is displayed on the display unit 11. The high voltage device 2 is arranged on the partition wall 102 in the operation room 101. This high voltage device 2 is provided with an operation panel including a display portion, an input button, etc., composed of a touch panel liquid crystal display, etc., and a switch for starting irradiation of X-rays. The high voltage device 2 is for setting the irradiation condition of X-rays, such as, e.g., the tube voltage and tube current of the X-ray tube 42 to be described later and the X-ray irradiation time.

The standing posture imaging stand 3 is provided with a lifting portion 34 for liftably supporting the X-ray detection unit 33. The X-ray detection unit 33 is also referred to as a bucky portion and is provided with an X-ray detector such as a flat panel detector (FPD) therein. The imaging unit 4 is provided with a base portion 46 movable in the orthogonal direction with respect to the ceiling of the imaging room 100, a support portion 45 extending downward from the base portion 46, and a movable portion 44 capable of being raised and lowered and pivoted with respect to the support portion 45. The movable portion 44 supports an X-ray tube 42 and a collimator 43. The X-ray tube 42 and the collimator 43 constitute an X-ray irradiation unit and are integrally movable. The collimator 43 constituting the X-ray irradiation unit is provided with a camera 41 as an image acquisition unit relating to the present invention for imaging the subject M.

The camera 41 is configured by a CCD camera or the like for capturing the visible image of the subject M. The camera 41 may be configured by a TOF (Time-Of-Flight) camera for capturing the range image of the subject M. Note that the TOF camera is also called a "TOF sensor" and is a camera for two-dimensionally obtaining the distance to a subject by converting the phase difference of light into a time difference and multiplying it by the velocity of light.

Figure 2:
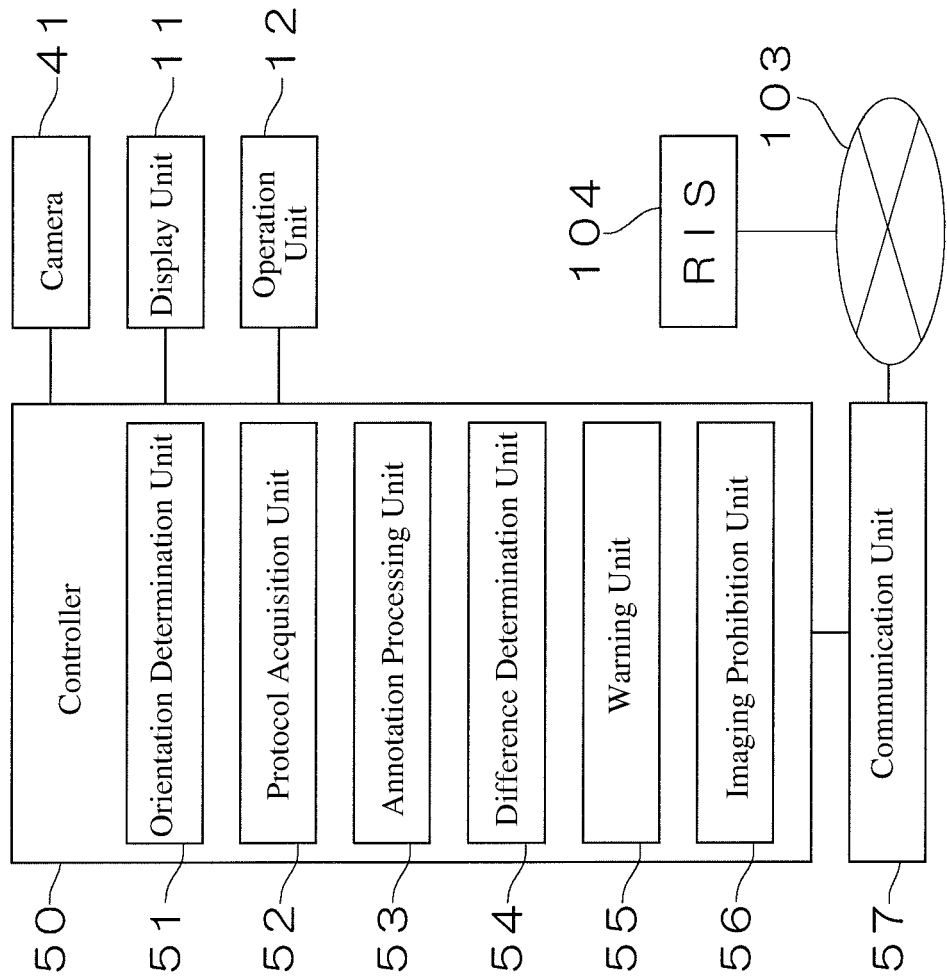
FIG. 2 is a block diagram showing a control system of an X-ray imaging apparatus according to a first embodiment of the present invention.

FIG. 2 is a block diagram showing the control system of the X-ray imaging apparatus according to the first embodiment of the present invention.

The X-ray imaging apparatus according to the first embodiment is provided with a controller 50. The controller 50 includes a CPU for executing logical operations, a ROM for storing operation programs required for controlling the apparatus, a RAM for temporarily storing data and the like at the time of the controlling, and the like. The controller 50 is configured by a computer with software installed. The function of each part included in the controller 50 is realized by executing the software installed on the computer.

The controller 50 is connected to the camera 41, the display unit 11, and the operation unit 12 described above. The controller 50 is connected to the radiological information system (RIS) 104, which is an in-hospital subject control system, via the communication unit 57 and the network 103 by a radio communication system such as Wi-Fi.

The controller 50 is provided with an orientation determination unit 51. The orientation determination unit 51 is configured to determine, from the visible image or the range image of the subject M acquired by the camera 41, whether the orientation of the subject M is an orientation for performing front imaging or an orientation for performing side imaging. The orientation determination unit 51 is configured to also determine whether the orientation for performing the front imaging is an orientation for performing AP (Anterior-Posterior) imaging or an orientation for performing PA (Posterior-Anterior) imaging. The orientation determination unit 51 is configured to also determine whether the orientation of the subject for performing the side imaging is an orientation for performing RL (Right-Left) imaging or an orientation for performing LR (Left-Right) imaging. The controller 50 is provided with a protocol acquisition unit 52 for acquiring and storing information, such as, the information on the subject M and the imaging protocol for the subject M, from the radiological information system 104. The controller 50 is provided with an annotation processing unit 53 for annotating a mark corresponding to the orientation of the subject M with respect to the X-ray image based on the orientation of the subject M determined by the orientation determination unit 51.

The controller 50 further includes a difference determination unit 54, a warning unit 55, and an imaging prohibition unit. The difference determination unit 54 is configured to determine whether the currently selected protocol among the protocols acquired by the protocol acquisition unit 52 and the orientation of the subject M determined by the orientation determination unit 51 are inconsistent with each other. The warning unit 55 is configured to issue a warning when the difference determination unit 54 determines that the currently selected protocol among the protocols acquired by the protocol acquisition unit 52 and the orientation of the subject M determined by the orientation determination unit 51 are inconsistent with each other. The imaging prohibition unit 56 is configured to prohibit X-ray imaging for the subject M when the difference determination unit 54 determines that the currently selected protocol among the protocols acquired by the protocol acquisition unit 52 and the orientation of the subject M determined by the orientation determination unit 51 are inconsistent with each other.

When performing X-ray imaging in the X-ray imaging apparatus having such a configuration, first, the radiologist operates the operation unit 12 of the console unit 1 shown in FIG. 1 to select a protocol for performing the X-ray imaging for the subject M from the protocols previously acquired by the protocol acquisition unit 52. Then, the radiologist makes the subject M stand at a position of the standing posture imaging stand 3 in front of the imaging unit 4 in a posture consistent with the protocol of the X-ray imaging.

In this state, the subject M is imaged with the camera 41 to acquire the visible image of the subject M or the range image of the subject M. Then, the orientation determination unit 51 determines, based on the acquired visible image of the subject M or the acquired range image of subject M, whether the orientation of the subject M is an orientation for performing AP (Anterior-Posterior) imaging or an orientation for performing PA (Posterior-Anterior) imaging for the front imaging, or whether the orientation of the subject is an orientation for performing RL (Right-Left) imaging or an orientation for performing LR (Left-Right) imaging for the side imaging. In this determination, an image of the facial region of the subject M, which is easy to extract a feature, is utilized. The orientation determination unit 51 determines the orientation of the subject M by using a neural network learned in advance. Then, the difference determination unit 54 determines whether the currently selected protocol among the protocols acquired by the protocol acquisition unit 52 and the orientation of the subject M determined by the orientation determination unit 51 are inconsistent with each other.

When the difference determination unit 54 determines that the currently selected protocol among the protocols acquired by the protocol acquisition unit 52 and the orientation of the subject M determined by the orientation determination unit 51 are consistent with each other, the X-ray imaging of the subject M is permitted. At this time, the radiologist performs the X-ray imaging with the imaging unit 4 by operating the high voltage device 2, etc. The annotation processing unit 53 annotates a mark corresponding to the orientation of the subject M with respect to the captured X-ray image. As a result, as shown in FIG. 9 to FIG. 13, a mark, such as, e.g., AP, PA, RL, and LR, is added to the lower right region of the X-ray image. At this time, since a mark consistent with the orientation of the subject M determined by the orientation determination unit 51 is given, an erroneous mark can be prevented from being given to the X-ray image.

On the other hand, when the difference determination unit 54 determines that the currently selected protocol among the protocols acquired by the protocol acquisition unit 52 and the orientation of the subject M determined by the orientation determination unit 51 are inconsistent with each other, the warning unit 55 issue a warning. This warning is performed by displaying a warning display on the display unit 11 of the console unit 1. Note that in addition to the warning display, a warning by sound or light may be performed. When the difference determination unit 54 determines that the currently selected protocol among the protocols acquired by the protocol acquisition unit 52 and the orientation of subject M determined by the orientation determination unit 51 are inconsistent with each other, the imaging prohibition unit 56 prohibits X-ray imaging of the subject M in addition to the warning. The warning and the imaging prohibition operation make it possible to assuredly prevent incorrect X-ray imaging from being performed.

Figure 3:
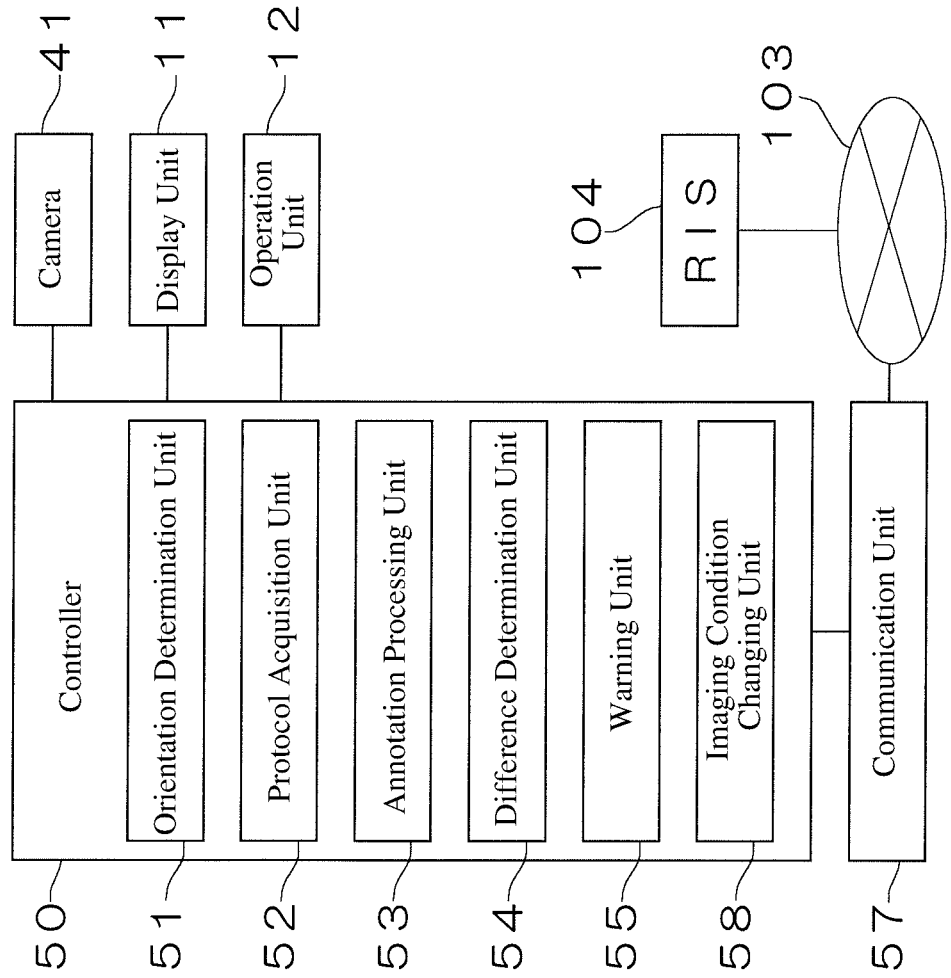
FIG. 3 is a block diagram showing a control system of an X-ray imaging apparatus according to a second embodiment of the present invention.

Next, another embodiment of the present invention will be described. FIG. 3 is a block diagram showing a control system of an X-ray imaging apparatus according to a second embodiment of the present invention. Note that the same members as those of the first embodiment shown in FIG. 2 are allotted by the same reference numerals, and the detailed descriptions thereof are omitted.

In the X-ray imaging apparatus according to the second embodiment, an imaging condition changing unit 58 is provided instead of the imaging prohibition unit 56 in the X-ray imaging apparatus according to the first embodiment. The imaging condition changing unit 58 is configured to change the X-ray imaging condition for the subject M when it is determined that the currently selected protocol among the protocols acquired by the protocol acquisition unit 52 and the orientation of the subject M determined by the orientation determination unit 51 are inconsistent with each other.

That is, in the X-ray imaging apparatus according to the second embodiment, when the difference determination unit 54 determines that the currently selected protocol among the protocols acquired by the protocol acquisition unit 52 and the orientation of the subject M determined by the orientation determination unit 51 are inconsistent with each other, in addition to the warning by the warning unit 55, the imaging condition changing unit 58 changes the imaging condition for performing the X-ray imaging to the imaging condition corresponding to the orientation of the subject M determined by the orientation determination unit 51, from the imaging condition corresponding to the currently selected protocol. This can prevent X-ray imaging from being performed under an erroneous imaging condition.

Figure 4:
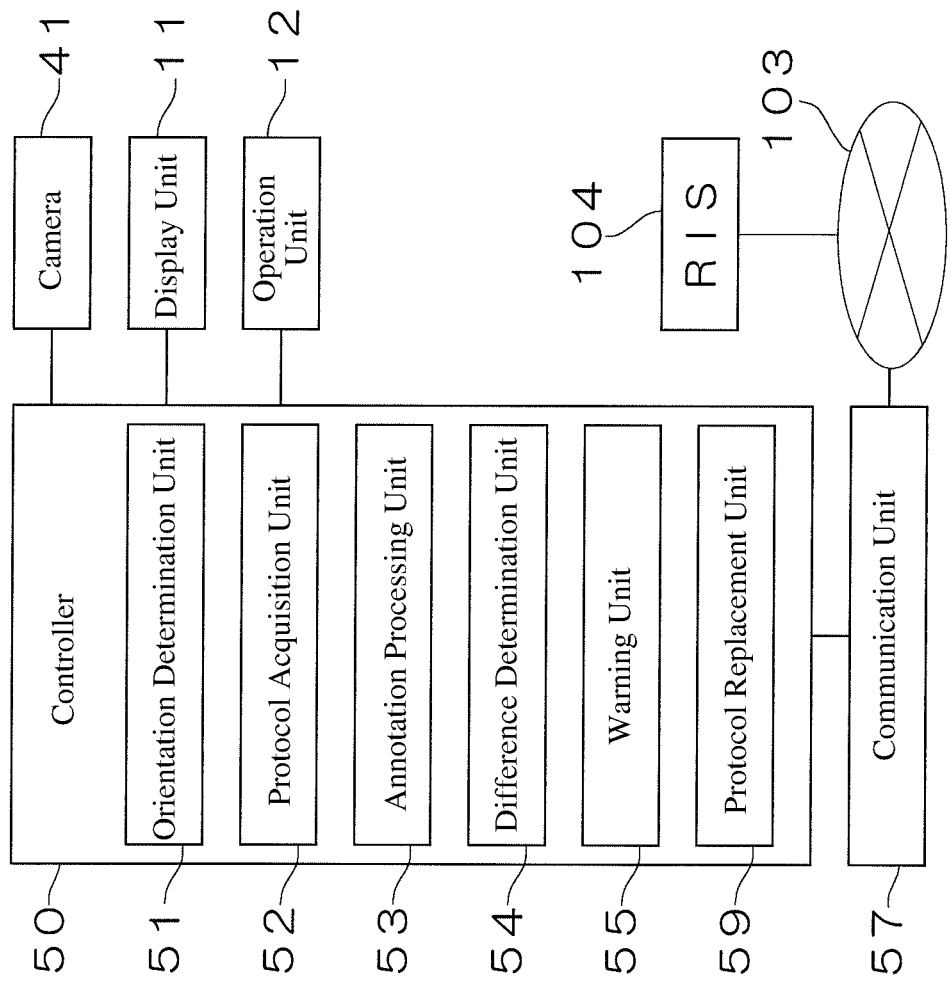
FIG. 4 is a block diagram showing a control system of an X-ray imaging apparatus according to a third embodiment of the present invention.
Figure 5:
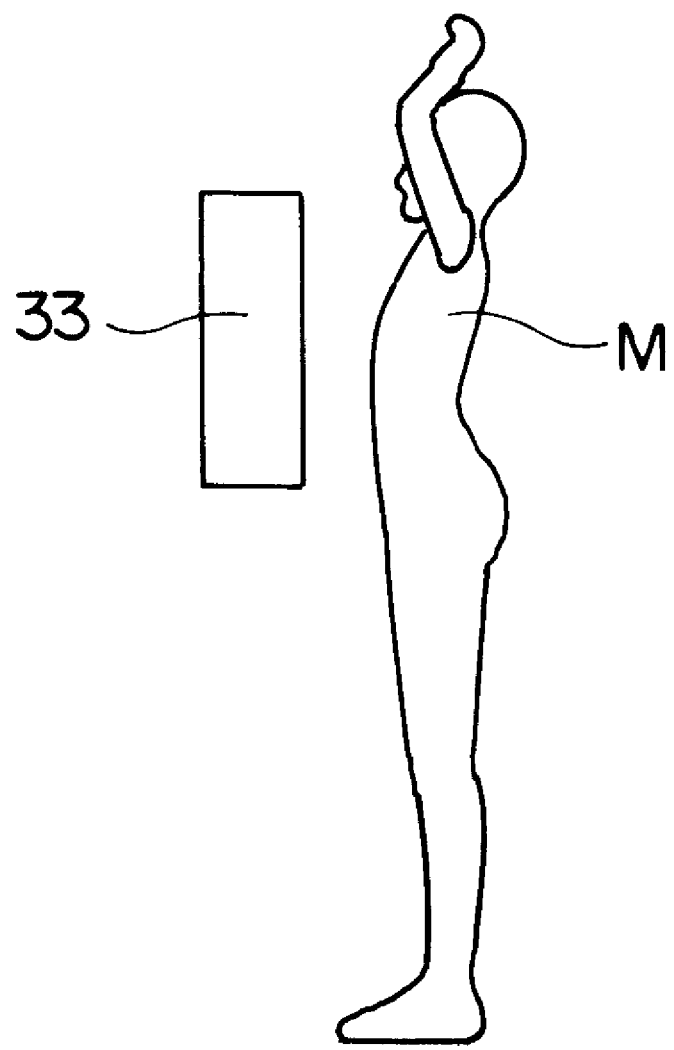
FIG. 5 is a schematic diagram showing a state of performing chest X-ray imaging for a subject M.
Figure 6:
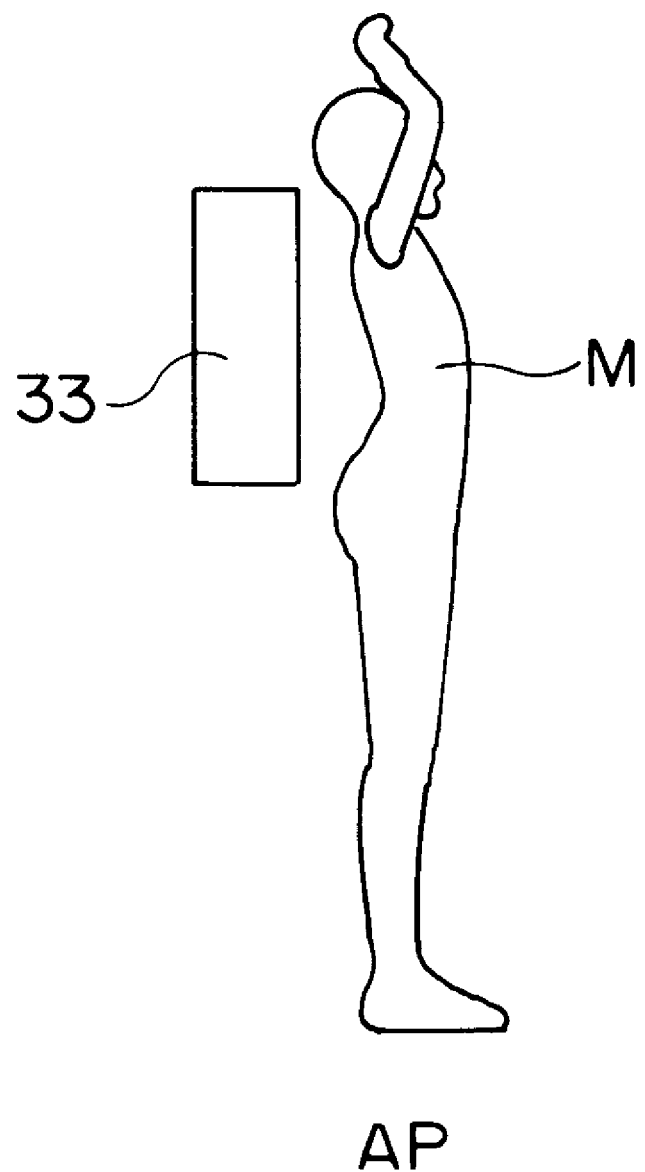
FIG. 6 is a schematic diagram showing a state of performing chest X-ray imaging for a subject M.
Figure 7:
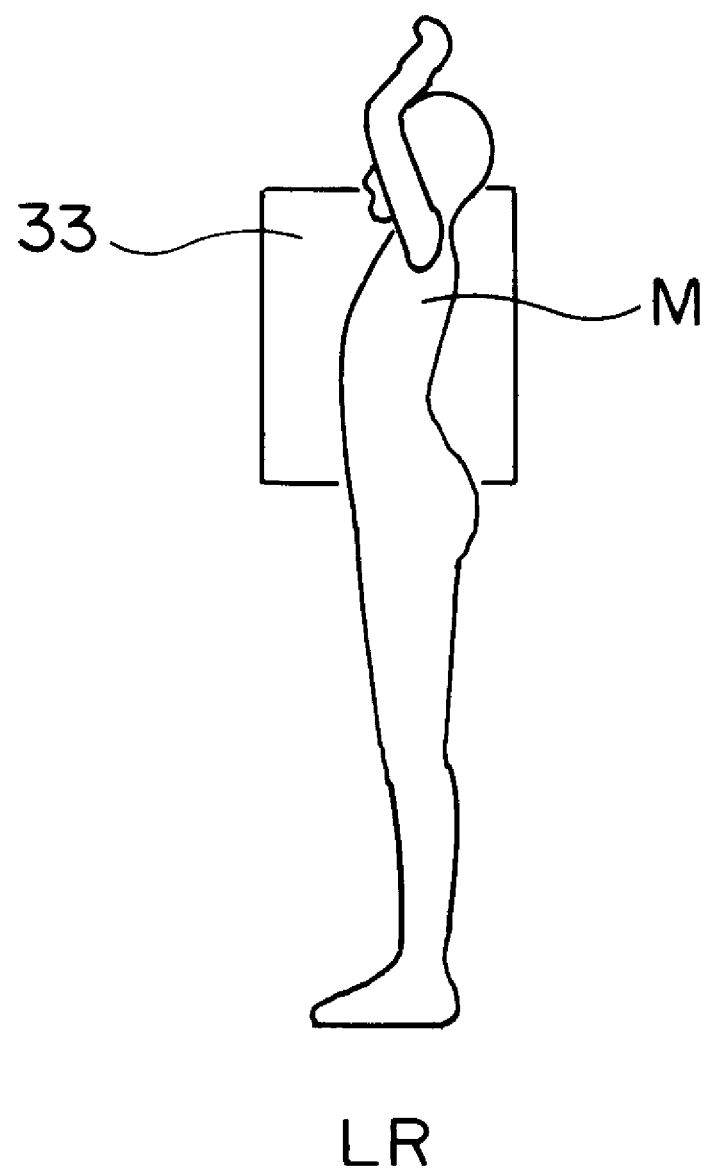
FIG. 7 is a schematic diagram showing a state of performing chest X-ray imaging for a subject M.
Figure 8:
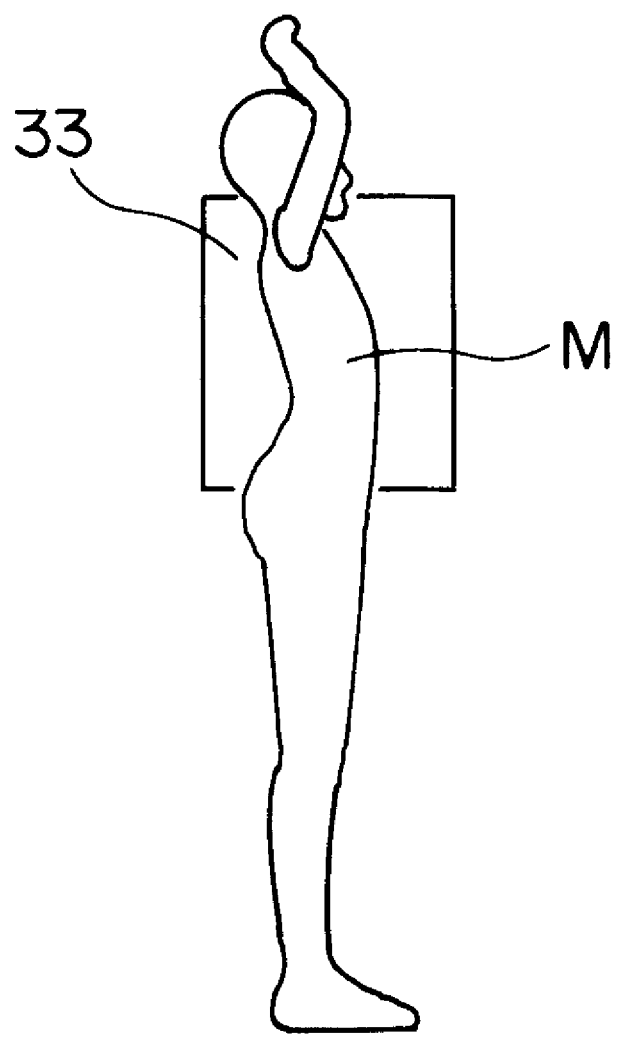
FIG. 8 is a schematic diagram showing a state of performing chest X-ray imaging for a subject M.
Figure 9:
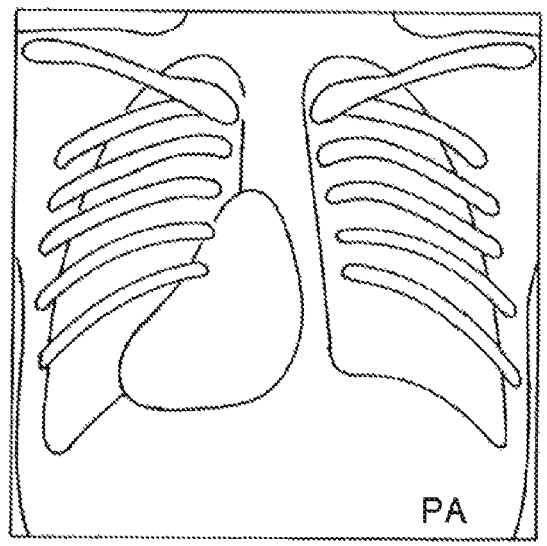
FIG. 9 is a schematic diagram showing an X-ray image taken with chest X-ray imaging.
Figure 10:
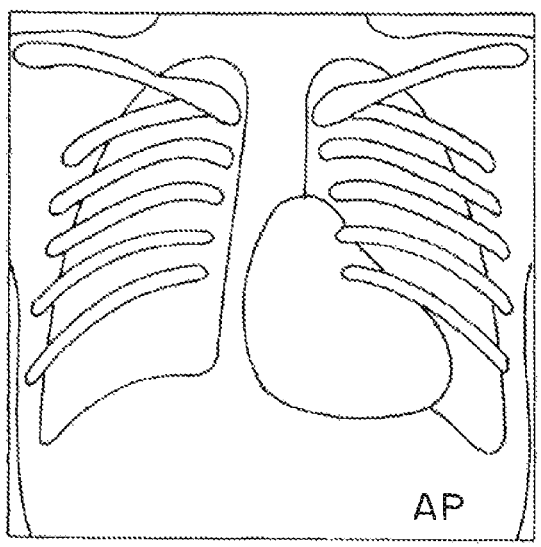
FIG. 10 is a schematic diagram showing an X-ray image taken with chest X-ray imaging.
Figure 11:
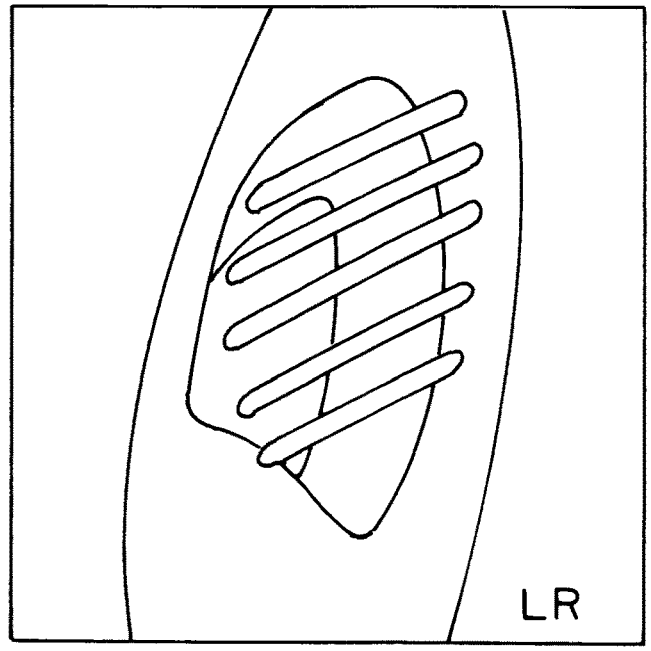
FIG. 11 is a schematic diagram showing an X-ray image taken with chest X-ray imaging.
Figure 12:
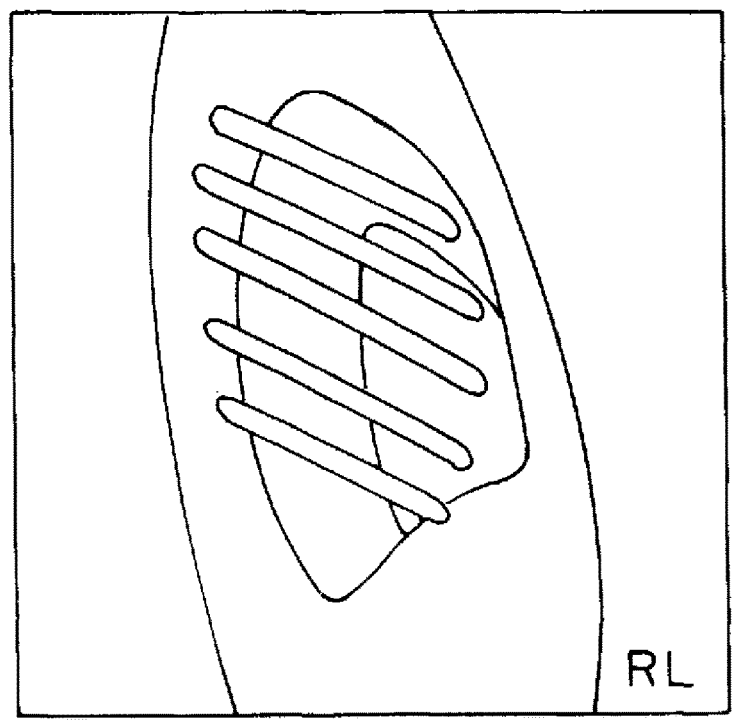
FIG. 12 is a schematic diagram showing an X-ray image taken with chest X-ray imaging.

Next, still another embodiment of the present invention will be described. FIG. 4 is a block diagram showing a control system of an X-ray imaging apparatus according to a third embodiment of the present invention. Note that the same members as those of the first and second embodiments shown in FIG. 2 and FIG. 3 are allotted by the same reference numerals, and the detailed descriptions thereof are omitted.

In the X-ray imaging apparatus according to the third embodiment, instead of the imaging prohibition unit 56 in the X-ray imaging apparatus according to the first embodiment, a protocol replacement unit 59 is provided. When it is determined that the currently selected protocol among the protocols acquired by the protocol acquisition unit 52 and the orientation of the subject M determined by the orientation determination unit 51 are inconsistent with each other, the protocol replacement unit 59 selects a protocol consistent with the orientation of the subject M determined by the orientation determination unit 51 of the protocol acquired by the protocol acquisition unit 52.

That is, in the X-ray imaging apparatus according to the third embodiment, when the difference determination unit 54 determines that the currently selected protocol among the protocols acquired by the protocol acquisition unit 52 and the orientation of the subject M determined by the orientation determination unit 51 are inconsistent with each other, in addition to the warning by the warning unit 55, the protocol replacement unit 59 discards the currently selected protocol, and instead, selects a protocol consistent with the orientation of the subject M determined by the orientation determination unit 51 among the plurality of protocols acquired by the protocol acquisition unit 52, and sets the imaging condition corresponding to the selected protocol. This can prevent X-ray imaging from being performed under an erroneous imaging condition.

At this time, in cases where all of the plurality of protocols acquired by the protocol acquisition unit 52 are inconsistent with the protocol consistent with the orientation of the subject M determined by the orientation determination unit 51, the warning unit 55 displays a warning indicating it.

Note that in the above-described embodiments, the descriptions have been made in which the present invention is applied to an X-ray imaging apparatus provided with a standing posture imaging stand 3 for performing X-ray imaging for a subject M in the standing state. However, the present invention may be applied to an X-ray imaging apparatus provided with a laying posture imaging table for performing X-ray imaging for a subject M in the lying position.

DESCRIPTION OF SYMBOLS

1: Console unit
2: High voltage device
3: Standing posture imaging stand
4: Imaging unit
11: Display unit
12: Operation unit
41: Camera
42: X-ray tube
43: Collimator
50: Controller
51: Orientation determination unit
52: Protocol acquisition unit
53: Annotation processing unit
54: Difference determination unit
55: Warning unit
56: Imaging prohibition unit
57: Communication unit
58: Imaging condition changing unit
59: Protocol replacement unit
100: Imaging room
101: Operation room
103: Network
104: Radiological information system
M; Subject

The invention claimed is:

1. A radiation imaging apparatus for producing a radiographic image of a subject, comprising:
    a radiation irradiation unit configured to irradiate the subject with radiation;
    a radiation detection unit configured to detect the radiation emitted from the radiation irradiation unit and passed through the subject;
    an orientation determination unit configured to determine that an orientation of the subject is which of an orientation for performing PA (Posterior-Anterior) imaging in which imaging is performed from behind of the subject, an orientation for performing AP (Anterior-Posterior) imaging in which imaging is performed from front of the subject, an orientation for performing LR (Left-Right) imaging in which imaging is performed from left of the subject, or an orientation for performing RL (Right-Left) imaging in which imaging is performed from right of the subject;
    a protocol acquisition unit configured to acquire an imaging protocol for the subject; and
    a difference determination unit configured to determine whether a currently selected protocol among protocols acquired by the protocol acquisition unit and the orientation of the subject determined by the orientation determination unit are inconsistent with each other.

2. The radiation imaging apparatus as recited in claim 1, further comprising:
    an annotation processing unit configured to annotate a mark corresponding to the orientation of the subject for an X-ray image, based on the orientation of the subject determined by the orientation determination unit.

3. The radiation imaging apparatus as recited in claim 1, further comprising:
    an image acquisition unit configured to acquire a visible image of the subject or a range image of the subject,
    wherein the orientation determination unit determines the orientation of the subject, based on the visible image of the subject or the range image of the subject acquired by the image acquisition unit.

4. The radiation imaging apparatus as recited in claim 3, wherein the image acquisition unit is attached to the radiation irradiation unit.

5. The radiation imaging apparatus as recited in claim 3, wherein the orientation determination unit determines the orientation of the subject by using a visible image of a face region of the subject or a range image of the subject acquired by the image acquisition unit.

6. The radiation imaging apparatus as recited in claim 1, further comprising:

a warning unit configured to issue a warning when the difference determination unit determines that the currently selected protocol among the protocols acquired by the protocol acquisition unit and the orientation of the subject determined by the orientation determination unit are inconsistent with each other.

7. The radiation imaging apparatus as recited in claim 1, further comprising:
an imaging prohibition unit configured to prohibit radiation imaging for the subject when the difference determination unit determines that the currently selected protocol among the protocols acquired by the protocol acquisition unit and the orientation of the subject determined by the orientation determination unit are inconsistent with each other.

8. The radiation imaging apparatus as recited in claim 1, further comprising:
an imaging condition changing unit configured to change a radiation imaging condition for the subject when the difference determination unit determines that the currently selected protocol among the protocols acquired by the protocol acquisition unit and the orientation of the subject determined by the orientation determination unit are inconsistent with each other.

9. The radiation imaging apparatus as recited in claim 1, further comprising:
a protocol replacement unit configured to select a protocol consistent with the orientation of the subject determined by the orientation determination unit among the protocols acquired by the protocol acquisition unit when the difference determination unit determines that the currently selected protocol among the protocols acquired by the protocol acquisition unit and the orientation of the subject determined by the orientation determination unit are inconsistent with each other.

10. The radiation imaging apparatus as recited in claim 9, wherein the protocol replacement unit issues a warning when there exists no protocol consistent with the orientation of the subject determined by the orientation determination unit among the protocols acquired by the protocol acquisition unit.

11. The radiation imaging apparatus as recited in claim 1, wherein the orientation determination unit determines the orientation of the subject by using a neural network.

12. A radiation imaging apparatus for producing a radiographic image of a subject, comprising:
a radiation irradiation unit configured to irradiate the subject with radiation;
a radiation detection unit configured to detect the radiation emitted from the radiation irradiation unit and passed through the subject;
an orientation determination unit configured to determine that an orientation of the subject is which of an orientation for performing PA (Posterior-Anterior) imaging in which imaging is performed from behind of the subject, an orientation for performing AP (Anterior-Posterior) imaging in which imaging is performed from front of the subject, an orientation for performing LR (Left-Right) imaging in which imaging is performed from left of the subject, or an orientation for performing RL (Right-Left) imaging in which imaging is performed from right of the subject; and
an annotation processing unit configured to annotate a mark corresponding to the orientation of the subject for an X-ray image based on the orientation of the subject determined by the orientation determination unit.

13. The radiation imaging apparatus as recited in claim 12, further comprising:
a protocol acquisition unit configured to acquire an imaging protocol for the subject; and
a difference determination unit configured to determine whether a currently selected protocol among protocols acquired by the protocol acquisition unit and the orientation of the subject determined by the orientation determination unit are inconsistent with each other.

14. The radiation imaging apparatus as recited in claim 13, further comprising:
a warning unit configured to issue a warning when the difference determination unit determines that the currently selected protocol among the protocols acquired by the protocol acquisition unit and the orientation of the subject determined by the orientation determination unit are inconsistent with each other.

15. The radiation imaging apparatus as recited in claim 13, further comprising:
an imaging prohibition unit configured to prohibit radiation imaging for the subject when the difference determination unit determines that the currently selected protocol among the protocols acquired by the protocol acquisition unit and the orientation of the subject determined by the orientation determination unit are inconsistent with each other.

16. The radiation imaging apparatus as recited in claim 13, further comprising:
an imaging condition changing unit configured to change a radiation imaging condition for the subject when the difference determination unit determines that the currently selected protocol among the protocols acquired by the protocol acquisition unit and the orientation of the subject determined by the orientation determination unit are inconsistent with each other.

17. The radiation imaging apparatus as recited in claim 13, further comprising:
a protocol replacement unit configured to select a protocol consistent with the orientation of the subject determined by the orientation determination unit among the protocols acquired by the protocol acquisition unit when the difference determination unit determines that the currently selected protocol among the protocols acquired by the protocol acquisition unit and the orientation of the subject determined by the orientation determination unit are inconsistent with each other.

18. The radiation imaging apparatus as recited in claim 17,
wherein the protocol replacement unit issues a warning when there exists no protocol consistent with the orientation of the subject determined by the orientation determination unit among the protocols acquired by the protocol acquisition unit.

19. The radiation imaging apparatus as recited in claim 12, further comprising:
an image acquisition unit configured to acquire a visible image of the subject or a range image of the subject,
wherein the orientation determination unit determines the orientation of the subject based on the visible image of the subject or the range image of the subject acquired by the image acquisition unit.

20. The radiation imaging apparatus as recited in claim 19,
wherein the image acquisition unit is attached to the radiation irradiation unit.

21. The radiation imaging apparatus as recited in claim 19, wherein the orientation determination unit determines the orientation of the subject by using a visible image of a face region of the subject or a range image of the subject acquired by the image acquisition unit.

22. The radiation imaging apparatus as recited in claim 12,
wherein the orientation determination unit determines the orientation of the subject by using a neural network.

* * * * *